United States Patent [19]

Taufen

[11] Patent Number: 4,477,573

[45] Date of Patent: Oct. 16, 1984

[54] SULPHUR GAS GEOCHEMICAL PROSPECTING

[75] Inventor: Paul M. Taufen, Golden, Colo.

[73] Assignee: Texasgulf, Inc., Stamford, Conn.

[21] Appl. No.: 383,028

[22] Filed: May 28, 1982

Related U.S. Application Data

[63] Continuation-in-part of Ser. No. 265,644, May 20, 1981, Pat. No. 4,377,640.

[51] Int. Cl.$^3$ .................. G01N 33/24; G01N 23/00
[52] U.S. Cl. ........................................ 436/33; 436/57; 436/133
[58] Field of Search .................... 436/31–33, 436/57, 133; 250/281, 505.1

[56] References Cited

U.S. PATENT DOCUMENTS

| | | | |
|---|---|---|---|
| 2,261,764 | 11/1941 | Horvitz | 436/33 |
| 2,330,716 | 9/1943 | Horvitz | 436/33 |
| 4,068,122 | 1/1978 | Schmidt et al. | 250/505.1 |
| 4,258,427 | 3/1981 | Favre et al. | 250/281 |
| 4,360,359 | 11/1982 | Oehler | 436/31 |

Primary Examiner—Michael S. Marcus
Attorney, Agent, or Firm—Bell, Seltzer, Park & Gibson

[57] ABSTRACT

A method of geochemical prospecting for buried sulphur mineralization which comprises collecting relatively organic free soil samples and determining the carbon isotope composition of the carbonate fraction.

7 Claims, 3 Drawing Figures

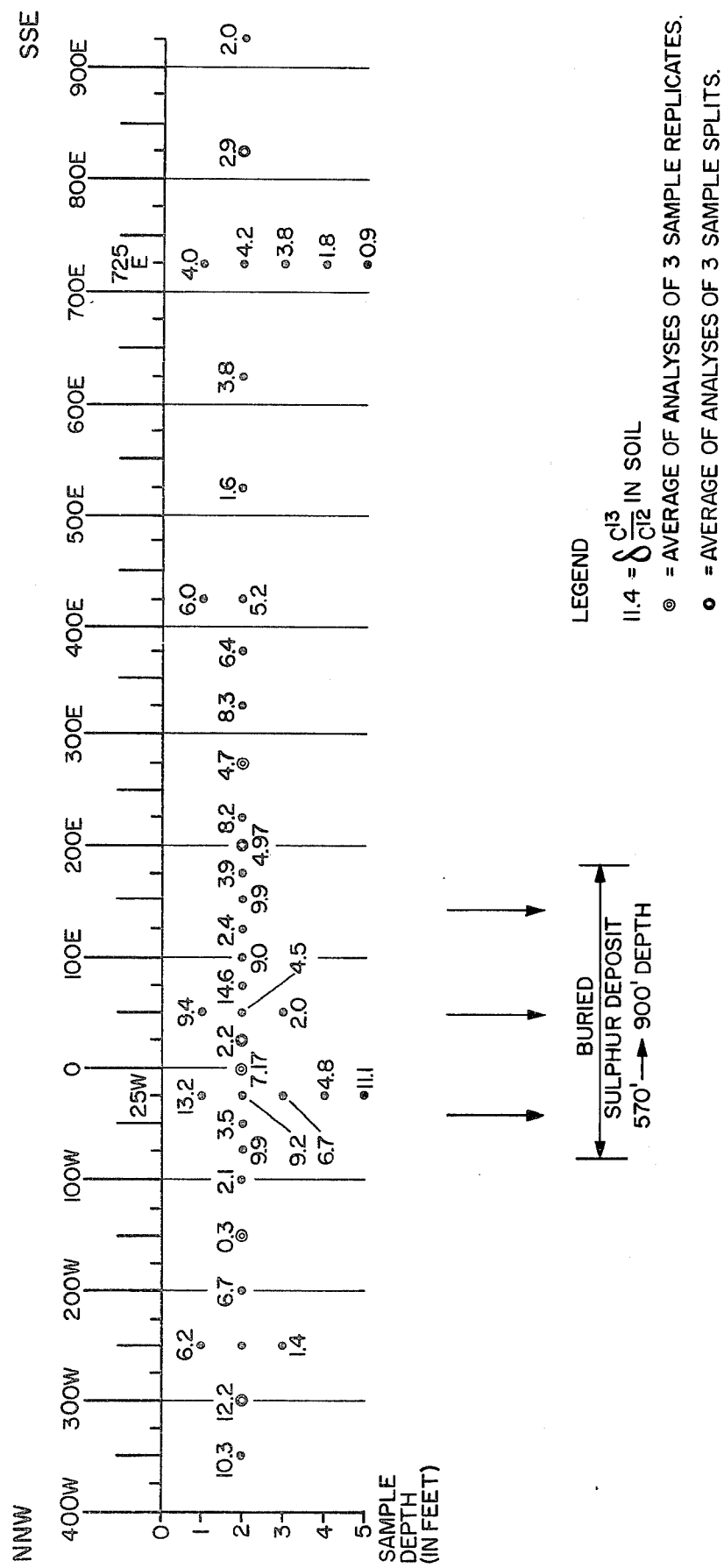

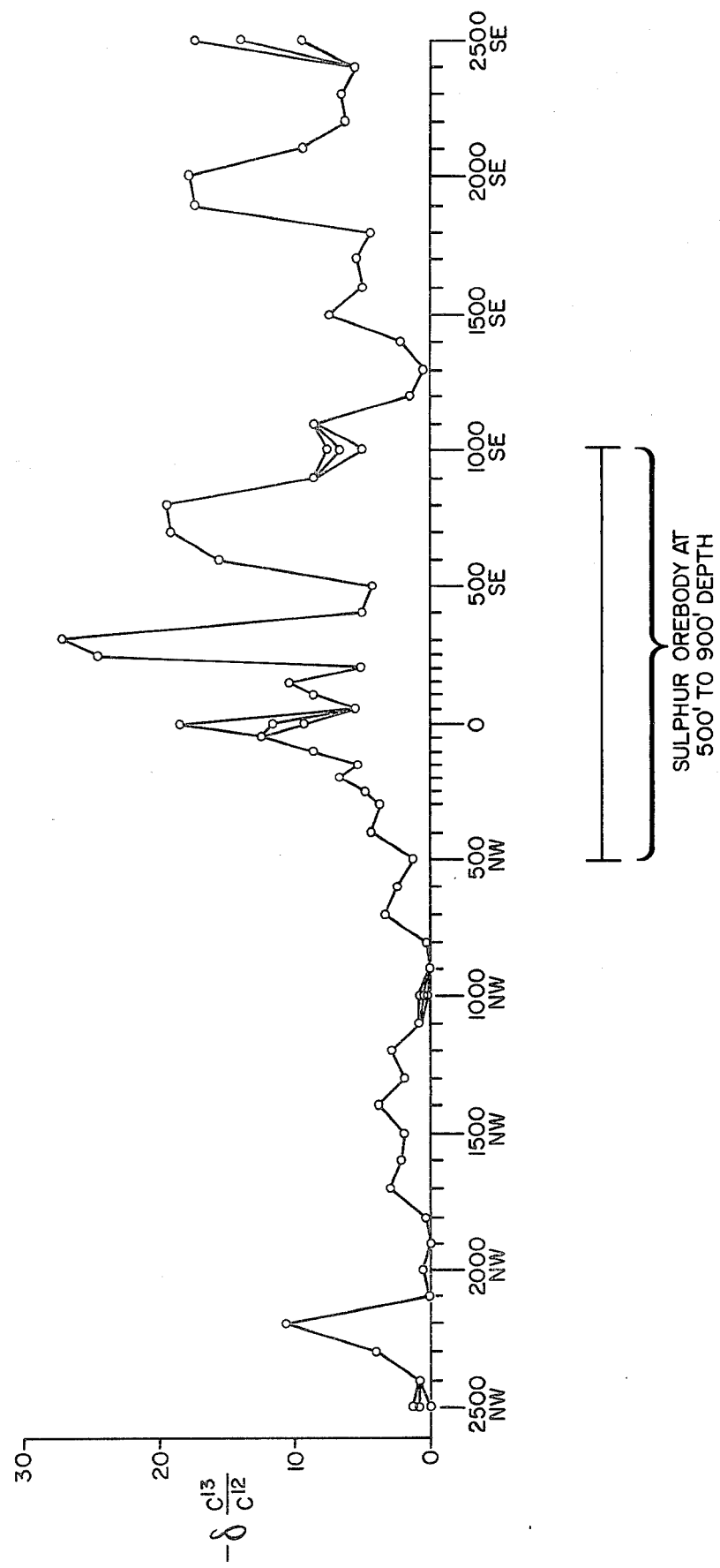

SULPHUR GAS GEOCHEMICAL PROSPECTING

CROSS-REFERENCE TO RELATED APPLICATION

This application is a continuation-in-part of my copending application Ser. No. 265,644, filed May 20, 1981 which issued as U.S. Pat. No. 4,377,640.

BACKGROUND OF THE INVENTION

1. Field Of The Invention

This invention relates to a method of geochemical prospecting for buried sulphur and sulphide mineralization, and, more particularly, to a method of collecting and analyzing soil samples to determine the presence of buried sulphur and sulphide mineralization.

2. Description Of The Prior Art

The field of carbon isotope geochemical prospecting is dominated by sample collection procedures recommending unspecified soil sampling depths. Publications dealing with petroleum prospecting applications make reference to "near surface soils" as optimum sample types and to the use of carbon isotopes in "Surface Geochemical Prospecting." Duchscherer, W., 1980, Geochemical Methods of Prospecting for Hydrocarbons, Oil and Gas Journal, Dec. 1, 1980; Duchscherer, W., 1979, Carbonates and Isotope Ratios from Surface Rocks—A Geochemical Guide to Underlying Petroleum Accumulation, Paper presented at Symposium II, "Unconventional Methods in Exploration for Petroleum and Natural Gas", Southern Methodist University, Dallas, Texas, Sept. 14, 1979.

There is nothing in the prior art which indicates that natural degradation of plant and organic matter and its conversion to mineral carbonate causes significant interference in carbon isotope prospecting surveys in the generation of carbon-12 enriched mineral carbonate indistinguishable from carbon-12 enriched mineral carbonate derived from buried petroleum reservoirs or sulphur deposits. There is also nothing in the prior art which indicates that soil depth is critical in establishing informative anomaly patterns in carbon isotope geochemical prospecting. The discussion of carbon isotope geochemistry in "Surface Geochemical Prospecting" (Geochemical Methods of Prospecting for Hydrocarbons, Ibid.) suggests to the carbon isotope prospector that optimum carbon isotope anomalies may be found at the ground surface.

SUMMARY OF THE INVENTION

It is an object of the present invention to describe a method of geochemical prospecting for buried sulphur mineralization.

A further object of the invention is to describe a method of collecting and analyzing soil samples to determine the presence of buried sulphur mineralization.

These and other objects are achieved by the provision of a method of geochemical prospecting for buried sulphur mineralization which comprises:

(a) collecting at least one soil sample from a depth beneath the zone of high plant and organic matter contribution to the composite soil;

(b) generating carbon dioxide gas from the carbonate fraction of said soil sample; and (c) analyzing the proportion of carbon-12 and carbon-13 in said carbon dioxide gas to determine the presence of buried sulphur mineralization.

BRIEF DESCRIPTION OF THE DRAWINGS

FIG. 2 is a graphical chart of Profile No. 1 shown in FIG. 1.

FIG. 3 is a graphical chart of Profile No. 2 shown in FIG. 1.

DETAILED DESCRIPTION OF THE INVENTION

Figure 1:
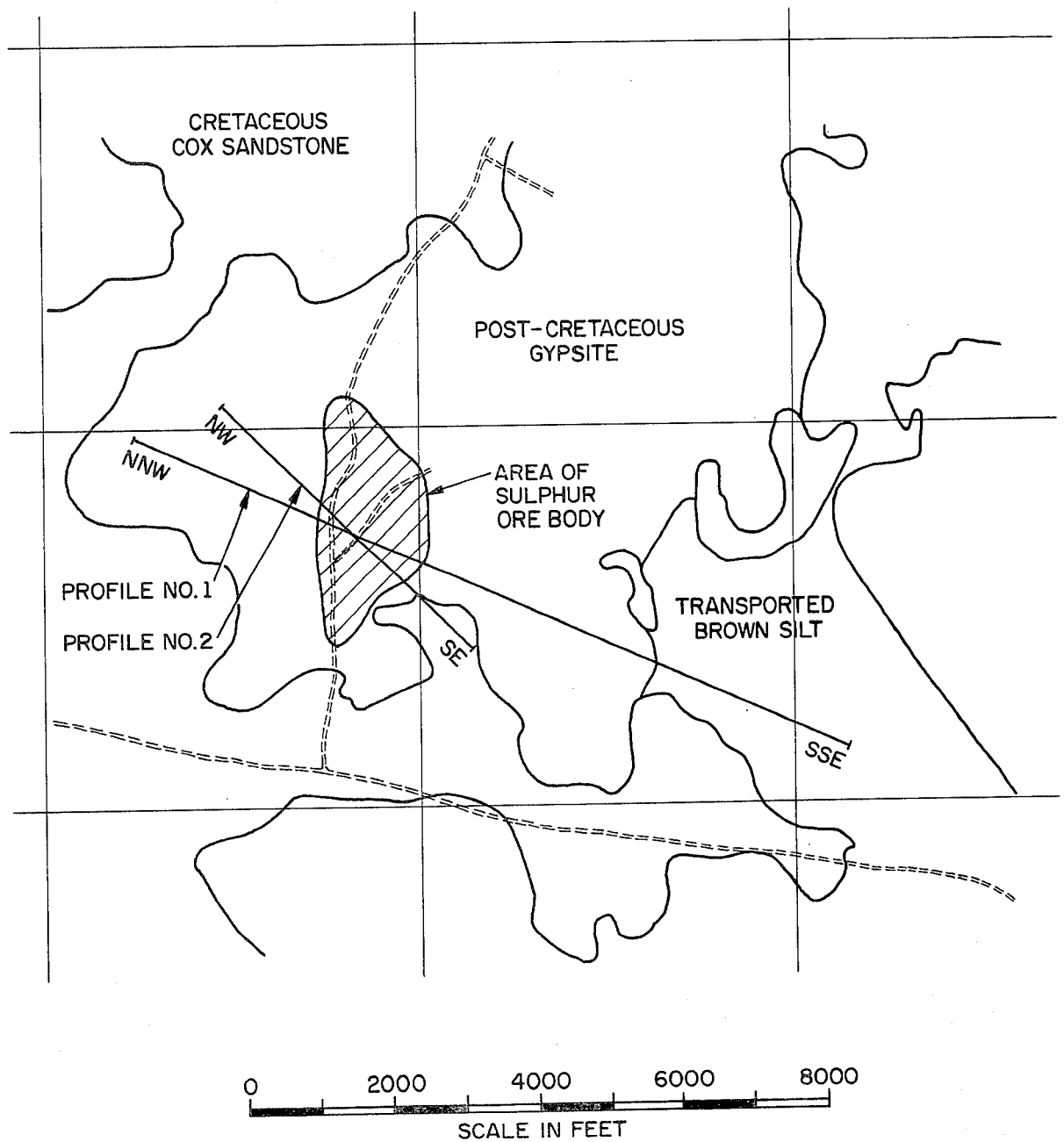
FIG. 1 is a schematic diagram illustrating the general geology and two geochemical profiles for the Union Sulphur Deposit in West Texas.

I have discovered that proper collection and handling of soil samples for carbonate carbon isotope analysis is critical in establishing optimum contrast between samples directly overlying buried mineralization and samples distant from buried orebodies. For example, at the Union Sulphur Deposit in west Texas, I have observed a direct relationship between soils enriched in carbon-12 and proximity to buried sulphur mineralization, with soils overlying sulphur ore enriched up to five fold versus background soils. At this location, soil sampling depth was discovered to be critical in determining carbon-12 enrichment patterns related to sulphur mineralization. I discovered, through the use of carbon-12, carbon-13 mass spectrometry, the importance of collecting soil samples beneath the upper soil horizons where decaying plant and organic matter contribute mineral carbonate to the composite soil. A series of soil samples collected at various depths showed a gradual decrease in the plant and organic matter contribution of carbon-12-enriched mineral carbonate with depth. A comparison of carbon-12, carbon-13 proportions in near surface soil collected directly over the Union Sulphur Deposit and in near surface soil collected at background locations indicates that carbon-12 enrichments occur in both near surface soils. The foregoing clearly indicates that decaying plant and organic matter produces some of the same carbon-12 enrichments caused by buried sulphur mineralization and that soils containing significant quantities of decaying plant and organic matter (i.e. near surface soils) are an inappropriate sample type for sulphur geochemical prospecting. I have discovered that only soil samples collected at a depth beneath the zone of high plant-organic matter contribution are capable of clearly reflecting buried sulphur mineralization.

FIG. 2 and FIG. 3 clearly illustrate the usefullness of collecting deep soil samples. In FIG. 2, site 725 E shows a gradual decrease with depth of carbon-12 content (plotted values are negative del values). This background sample is distant from the sulphur ore and the significant carbon-12 concentration in the top 3 feet of soil are attributed to mineral carbonate formed by conversion of plant and organic matter. In FIG. 2, site 25 W exhibits a pattern in the upper 3 feet of soil similar to that of site 725 E; however, the 5 foot 5 foot depth sample exhibits an increased carbon-12 concentration attributable to leakage from the buried sulphur mineralization underlying site 25 W. FIG. 3 illustrates an entire line profile using an 8 to 10 foot sampling depth interval. This deep soil sampling profile is characterized by lower background values, better anomaly contrast and a more informative anomaly pattern. The improved resolution shown in FIG. 3 is due to the effective elimination of noise from contributed mineral carbonate derived from plant and organic matter and to the enhancement of signal from leakage associated with buried sulphur mineralization (i.e. sulphur mineralization refers to sulphur and carbonate). FIG. 3 clearly indicates the advantages of collecting soils from beneath the zone of plant and organic matter contribution to the composite soil.

The method of the present invention is further illustrated in the following non-limiting example:

EXAMPLE

Soil samples over three case study areas (i.e. Union Sulphur Deposit, Maverick Draw Deposit, and Saddle Butte Deposit) in west Texas were collected by using either an air rotary hydraulically operated Winkie drill with a small bi-cone bit or by using a compressed-air/-hydraulic air track sampler with a cross bit. Cuttings from the 9' to 11' interval or from the 8' to 10' interval were collected, labeled, and shipped to Coastal Science Laboratories in Port Aransas, Texas for carbon isotope determinations. Physical descriptions, mineralogical descriptions and degree of effercescence with dilute hydrochloric acid were recorded for each sample.

Statistical control in each survey consisted of monitoring carbon isotope composition difference due to sampling error and carbon isotope composition differences die to analytical error according to a prescribed method. See, for example, Misch, A. T. et al; Geochemical Survey of Missouri-Methods of Sampling, Laboratory Analysis, and Statistical Reduction of Data, U.S.G.S. Professional Paper 954-A. Analyses of three replicate samples from each of numerous sample sites indicated minor sampling error associated with the sampling technique. Replicate sample analyses plotted on sampling profile lines indicated that carbon isotope composition differences between sulphur mineralization related samples and background samples greatly exceeded carbon isotope composition differences within individual sample sites. Sampling error was found to be about $\pm 1\delta$ C13/C12 unit. The $\delta$ C13/C12 values were calculated according to the following equation and reported as "per mil" values:

$$\delta C13/C12 = \frac{\frac{C13}{C12} \text{ (sample)}}{\frac{C13}{C12} \text{ (standard)}} - 1 \times 1000,$$

where a belemnite fossil from the Peedee formation in South Carolina is used as the standard. Faure, 6., 1977, Principles of Isotope Geology, John Wiley & Sons, New York. Analytical error determined by succesive analyses of individual samples yielded an error of $\pm 0.5\delta$ C13/C12 unit. The combined sampling and analytical error associated with the survey of $\pm 1.5\delta$ C13/C12 units is much lower than the differences of 12 or more $\delta$ C13/C12 units between sulphur mineralization related samples and background samples. The mineralization related anomalies are therefore real, and not merely statistically random anomalies die to combinations of sampling and analytical errors.

I claim:
1. A method of geochemical prospecting for buried sulphur mineralization which comprises:
    (a) collecting at least one soil sample from a depth beneath the zone of high plant and organic matter contribution to the composite soil;
    (b) generating carbon dioxide gas from the carbon in the carbonate fraction of said soil sample; and,
    (c) analysing the proportion of carbonate carbon-12 and carbonate carbon-13 in said carbon dioxide gas to determine the presence of buried sulphur mineralization.

2. A method according to claim 1, wherein said buried sulphur mineralization is sulphur ore.

3. A method according to claim 1, wherein analyzing the porportion of carbon-12 and carbon-13 in said carbon dioxide has is accomplished by mass spectrometry.

4. A method according to claim 1, wherein said proportion of carbon-12 and carbon-13 in anomalous samples is at least two del units greater than the background.

5. A method according to claim 1, wherein said buried sulphur mineralization is a sulphide deposit.

6. A method according to claim 1, wherein said carbon dioxide gas is generated by treating said soil sample with an acid.

7. A method according to claim 6, wherein said acid is phosphoric acid.

* * * * *